United States Patent [19]

Tanaka et al.

[11] 4,113,434
[45] Sep. 12, 1978

[54] METHOD AND APPARATUS FOR COLLECTIVELY SAMPLING A PLURALITY OF GASEOUS PHASES IN DESIRED PROPORTIONS FOR GAS ANALYSIS OR OTHER PURPOSES

[75] Inventors: Shinzo Tanaka, Osaka; Shinichi Tsubamoto, Kyoto; Koichi Yamashita; Tadashi Eguchi, both of Nara; Kashirou Inoue, Osaka, all of Japan

[73] Assignee: Yanagimoto Seisakusho Co., Ltd., Kyoto, Japan

[21] Appl. No.: 709,088

[22] Filed: Jul. 27, 1976

[30] Foreign Application Priority Data

Jul. 30, 1975 [JP] Japan .................................. 50-93741
Jul. 31, 1975 [JP] Japan .................................. 50-94620

[51] Int. Cl.$^2$ ............................................. G01N 1/22
[52] U.S. Cl. ............................... 23/232 R; 23/232 E; 73/23; 73/421.5 R; 422/94; 422/93
[58] Field of Search ............. 23/232 R, 232 E, 254 R, 23/254 E, 255 R, 255 E; 73/421.5 R, 421.5 A, 23

[56] References Cited

U.S. PATENT DOCUMENTS

| 2,846,121 | 8/1958 | Ronnebeck | 23/254 R |
| 3,298,786 | 1/1967 | Hinsuark | 23/254 R X |
| 3,425,807 | 2/1969 | Levy | 23/254 R |
| 3,535,084 | 10/1970 | Izawa et al. | 23/254 R |
| 3,607,073 | 9/1971 | Stamm | 23/254 R X |
| 3,753,653 | 8/1973 | Brieva | 23/254 R X |

Primary Examiner—R.E. Serwin
Attorney, Agent, or Firm—Morgan, Finnegan, Pine, Foley & Lee

[57] ABSTRACT

A continuous sampling flow consisting of a plurality of gases is provided. The sampling of a plurality of gases according to the present invention comprises separately forming continuous gas streams of different gaseous phases, discharging said gas streams simultaneously and continuously into a common definite space in such a manner as to prevent them from mixing together, and sequentially positioning an inlet of open-sampling means successively in said discharged gas streams so that the gases in the individual gas streams are successively sampled and that a single stream formed by the sampled gases from the individual gas streams being in series one after another is taken out. In a preferred embodiment of the invention, the amount of gas sampled from each of said discharged gas streams is such that it will not disturb the discharged gas streams, e.g., it is one-half or less of the amount of flow of gas stream to be sampled, while the remaining gases in the individual gas streams are collectively exhausted through pressure control means, as desired. In the case of a gas analysis, said sampled single gas stream is supplied to a detector, which, therefore, will produce signals each corresponding to one of said gases. From these signals it is possible to know the concentrations of particular components of the individual gases.

37 Claims, 13 Drawing Figures

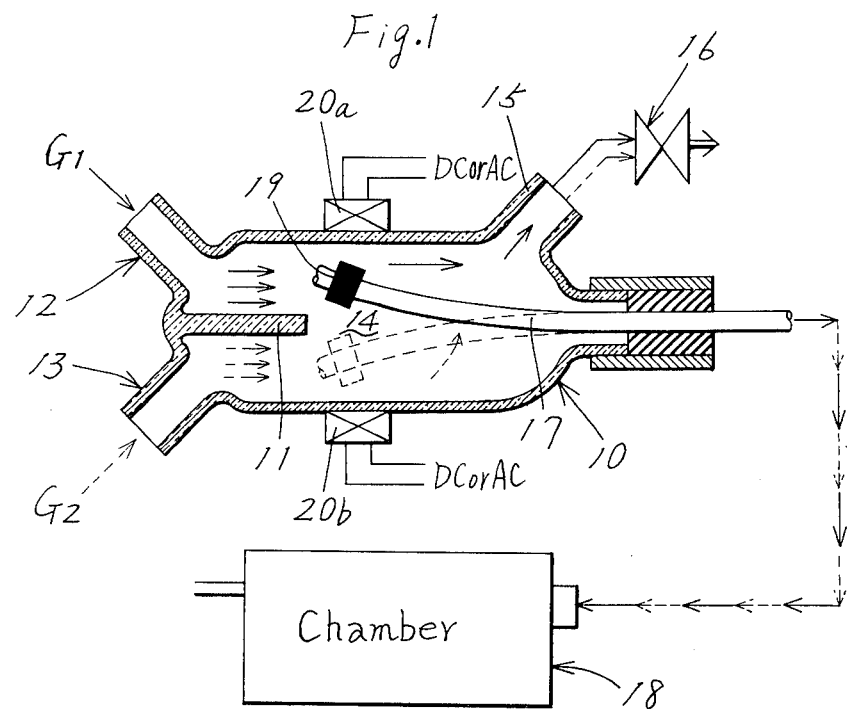
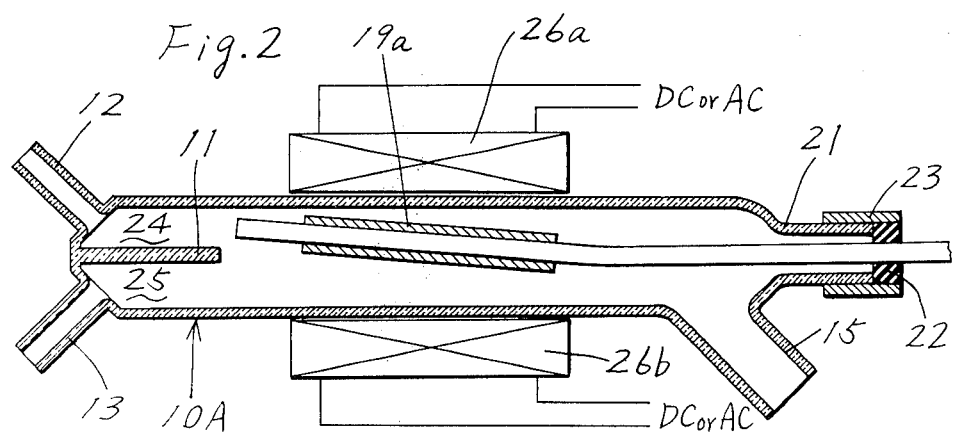

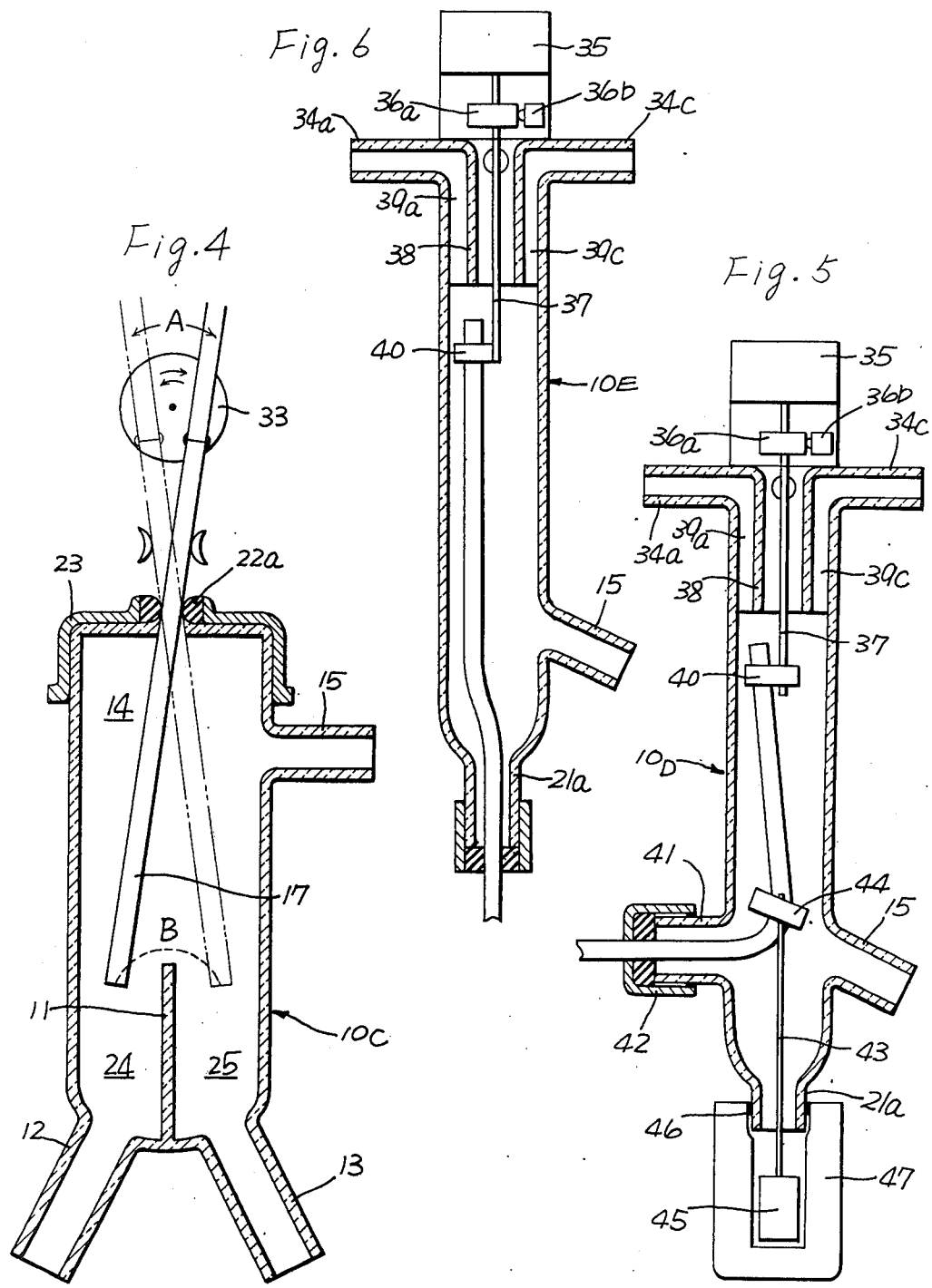

METHOD AND APPARATUS FOR COLLECTIVELY SAMPLING A PLURALITY OF GASEOUS PHASES IN DESIRED PROPORTIONS FOR GAS ANALYSIS OR OTHER PURPOSES

BACKGROUND OF THE INVENTION

The present invention relates to a method and apparatus for sampling a plurality of gases and analyzing or otherwise treating the sampled gases, and more particularly to a flow-chopping method and apparatus wherein a plurality of gases are collectively and sequentially sampled in desired proportions for gas analysis or other purposes.

For quantitative dilution, mixing or replacement of gases or for switching between zero reference gas and sample gas, a multi-channel valve is usually used. The individual gases supplied to the multi-channel valve from their gas supply sources through respective flow control valves are guided through the outlet passage of said valve to a take-out channel extended therefrom when the corresponding supply channels are opened by the mechanical channel-switching of said valve. With such channel-switching system, however, a transient pressure change occurs upon opening and closing of the channels in the switching valve, such pressure change, coupled with the complexity of individual adjustment of the gas supply channels, making it difficult to achieve the correct control of the amount of each gas. Further, in gas analysis the repeated opening and closing of channels for individual gases results in said gases being adsorbed at some portion of the flow system and each such adsorbed gas being removed by other gases, so that the base and signal values corresponding to zero reference gas or span gas and sample gases respectively become incorrect, and a substantial amount of time is expended before they are stabilized. On the other hand, in a gas analysis which does not need the switching of channels, although there are no problems caused by the above-mentioned transient pressure change or adsorption of gas by the flow system, inherent problems due to the use of a plurality of channels for sample and reference gases do arise.

Thus, a construction in which a detector consists of a sample cell and a reference cell, for example, a pair of heat conductivity cells or a non-dispersed infrared analyzer is supplied or charged with a compensation gas or reference gas for setting in the reference cell a zero level reference for signal values, and the detector produces as its output a signal which corresponds to the value of sample gas minus the value of reference gas, so that relatively accurate quantitative analysis can be carried out. However, the accuracy and the stability of sample and reference cells are fixed by the inherent characteristics of these cells and by the arrangement of gas channels and of the optical system, and intrinsic errors resulting therefrom cannot be eliminated.

In other detection systems, such as a flame ionization-detector and a chemiluminescence detector for deriving a signal only concerning one gas, if an arrangement intended to simultaneously detect at least two gases is employed the above drawback should become more noticeable. More specifically, in such cases, a photochemical or physical excitation-reactor must be provided for each of the gases, and it is very difficult to equalize the conditions of these reactors.

We have investigated the various drawbacks in the gas analyzing system described above, which handle a plurality of gases, and we have come to the conclusion that if different gases one of which may be a zero reference gas are successively taken-out of the streams of the gases little by little and fed as a series gas stream into a detection-cell, excitation-chamber or other chamber, then the foregoing absorption and decomposition problems about a multi-channel valve will disappear and a detected value for each gas which repeatedly appears can be obtained at the detector, contributing much to the stablization of gas analysis and the collective measurement of different samples. If such gas analyzing system is used, it is also clear that a two-cell system for sample and reference gases may be replaced by a single cell to compare two gases therein, so that the error due to cell conditions can be eliminated.

SUMMARY OF THE INVENTION

Therefore, it is an object of the invention to provide a novel method and apparatus enabling of gaseous to be sampled in a single sampling line, without using any channel switching valve, for a system which simultaneously uses a plurality of gases.

Another object of the invention is to provide a method and apparatus for collectively sampling a plurality of gases by a sampling line adapted to be driven for accurately setting the sample proportions of individual gases without reporting to the individual pressure or flow control of the gas supply sources or supply lines.

A further object of the invention is to provide a novel method and apparatus for collectively sampling a plurality of gases in such a manner that the sampled gases are formed into the series of gases which is continuously fed to an intended device through a single channel.

A still further object of the invention is to provide a novel method and apparatus for gas analysis, wherein a series gas stream consisting of a plurality of sampled gases is fed to a single detector, whereby the accurate relative values for the respective gases can be detected.

Briefly, in the system for collectively sampling a plurality of gases according to the present invention, a plurality of continuous gas streams are laid together in a common defining space in such a manner as to prevent the gas streams from substantially mixing with each other, while said gas streams are successively and cyclically sampled by a single sampling conduit which can move within said space to position the inlet portion thereof, one by one, in all of the gases in the sampled gas series being fed to a mixer, diluter, detector or the like connected to the downstream end of said sampling conduit. In gas analysis, the series of gases sampled as described above are received by the detector which then provides output signals corresponding to the respective gases. Therefore, it is possible to determine the physical and chemical values such as the concentration of a particular component in each of these gases.

In this method, if the value corresponding to a particular gas among said plurality of cyclically detected values is used as the zero level reference, then the values of the other gases relative to the reference in the same cell can be obtained, thus solving the above-mentioned problem of errors in the two-cell system.

Further, when the rate of sampling from each gas stream by said sampling conduit is restricted to about ½ or less and preferably to about ⅓ of the flow of corresponding stream, there will be no intermission of the individual continuous gas streams whether the press-in sampling method or the suction sampling method is employed. Therefore, although, at a time for changing the sampling position from one of the streams to another a little mixing of the gas from the one stream with the gas from the next stream may take place in the sampling conduit to some extent, the respective gases out of the streams will flow as successive gaseous masses therethrough substantially at a constant pressure and in fixed amounts, so that it is possible to derive measured value representing each of the gas streams under the same conditions.

The apparatus for collectively sampling a plurality of gases according to the invention comprises means for continuously discharging a plurality of different gases in parallel relation to each other, a common channel or ventilated chamber communication with said discharging means for receiving all the parallel stream of discharged gases, a movable sampling tube having an inlet opened toward the upstream and adapted to be positioned successively in each of said streams within said ventilated chamber, and a surplus-gas vent formed in the downstream portion of said ventilated chamber.

Such apparatus of the present invention will be hereinafter referred to as "flow chopper" in consideration of its similarity to an optical chopper in which a sector successively selects a plurality of optical paths.

If suitable pressure control means (e.g., a pressure regulating valve) is connected to said surplus gas exhaust port of the flow chopper, the adjustment of said means makes it possible to control the pressure and the rate of flow of the gases being sampled without changing the supply pressure and the rate of flow of the individual gases. In addition, the sampling ratio of gases can be easily set by adjusting the residence time of the sampling tube inlet at the individual gas streams.

The drive of the sampling tube can be effected by a motive power source or by magnetic actuating means located substantially outside said channel chamber and operatively connected to said tube. Preferably, the sampling tube employed is made of a heat-resistant flexible tube, e.g., a Teflon tube having a cross-sectional area sufficiently smaller than, or preferably about 1/20 or less of, the cross-sectional area of each gas stream. One end of said tube or a suitable intermediate region thereof is fitted in and fixed to a take-out port formed in said chamber, while the other or free end thereof located in the chamber is used as a sampling entrance and swung or revolted so as to be brought to the gas sampling positions. With such construction, it is possible to provide a simple and highly efficient flow chopper wherein the load which must be supported by above driving means disposed outside the chamber is very small while there is no danger of the fluid-leakage at the movable portion of the sampling tube.

Other objects, aspects and advantages of the present invention than those described above will appear from the following detailed description taken in conjunction with the accompanying drawings. It is to be understood, however, that the method and apparatus of the present invention are not restricted to the preferred embodiments shown in the accompanying drawings and that various changes and modifications may be made within the spirit and scope of the invention as defined by the appended claims.

BRIEF DESCRIPTION OF THE DRAWINGS

FIG. 1 is a schematic diagram illustrating the principle of the present invention;

FIGS. 2 - 4 show longitudinal sections of two-inlet flow choppers constructed according to the invention;

FIGS. 5 and 6 show longitudinal sections of multi-inlet flow choppers constructed according to the invention;

DETAILED DESCRIPTION OF THE INVENTION

Figure 3:
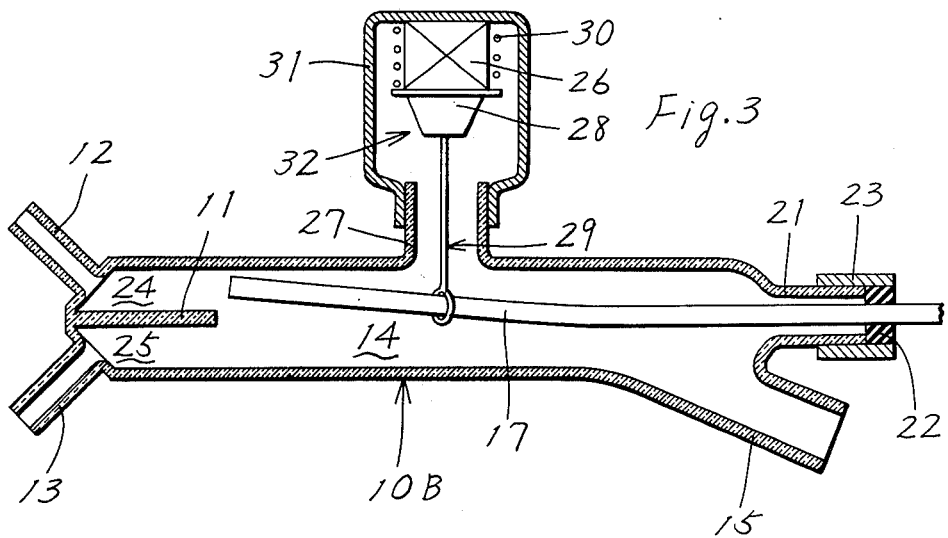

Referring to FIG. 1, there is shown a basic construction of the flow chopping system for sampling and utilizing a plurality of gaseous phases according to the present invention. In FIG. 1, the reference numeral 10 designates a flow chopper for successively and cyclically sampling gases from a plurality of gas streams. The flow chopper 10 comprises a cylinder-like body having therein a partition plate 11 extending from one end of the body, shown on the left-hand side of this Figure, preferably in the direction of the cylinder axis to define a plurality of, or two in this case, independent gas streaming channels, inlet ports 12 and 13 on the end wall communicated to the respective gas streaming channels, so that gases G1 and G2 introduced from the inlet ports are discharged through the channels into a cylinder chamber 14 occupying at the downstream side of the channels the major port in the cylinder in such a manner that they do not become substantially mixed together. In the flow chopper 10, in order that the cylinder chamber 14 may function as a ventilated constitution for a plurality of gas streams, there is provided a gas vent or exhaust port 15 adjacent the downstream end for exhausting gas streams at all times. Designated at 16 is a pressure regulating valve connected to the exhaust port 15, whereby the pressure in the chamber 14 is controlled. A movable sampling tube 17 is fluid-tightly inserted into the body of the flow chopper 10 and it is so arranged that when the sampling tube 17 is brought to any one of its fixed positions within its moving range, its inlet opening at the one end thereof within the chamber is disposed facing toward upstream just behind the associated independent gas streaming channel so as to receive the gas of this stream alone. The downstream end of the sampling tube 17 outside the chopper is connected to a detector, mixing chamber or other gas utilizing chamber 18 directly or through a suitable pipeline, so that fractions of the gases G1 and G2 shown in full and dotted lines, respectively, in FIG. 1 are alternately and continuously fed into said chamber 18. If the chamber 18 is a gas detector, therefore, such detector will alternately generate signals corresponding to said gas fractions, thus providing for various gas analyses to be later described. If the chamber 18 is a mixing chamber, since the gases G1 and G2 are alternately fed in fractions into the chamber, mixing can be rapidly effected within the chamber to form a uniform mixture of gases. Further, the gas mixing ratio in this case can be accurately set in a wide range by selecting the appropriate residence time for the sampling tube 17 with respect to each sampling position in the flow chopper 10. If the chamber is a diluter, such useful function will also be helpful for the dilution of gas.

As will be later described in detail, various mechanisms may be employed to drive the movable sampling tube 17. The driving mechanism schematically shown in FIG. 1 comprises a magnetic element or desirably a polarized element 19 mounted on the front end periphery of the movable sampling tube 17, and magnetic poles 20a and 20b mounted on the outer surface of the cylinder 10 facing respectively the parallel halves of the chamber extending through the two inlet gas streaming channels, said magnetic poles serving to alternately repel and attract the magnetic element 19.

Preferred embodiments of the flow chopper according to the invention are shown in FIGS. 2–6. In these embodiments, the cylinder generally designated at 10 as the body of the flow chopper is formed of glass or plastics such as acrylic resin, while the sampling tube 17 is formed by a fine tube desirably of a heat-resistant flexible material, such as Teflon tube. The sampling tube 17 is inserted into the cylinder 10 through an opening 21 formed in the end of the chopper cylinder 10 opposite to its streaming channels. Fitted in the opening 21 is a ring 23 having a packing member 22 for fluid-tightly holding the Teflon tube 17. The only flow chopper in which the sampling tube and the manner of its insertion into the chopper cylinder may be different from the above is shown in FIG. 4, however, this will be later described.

The flow choppers shown in FIGS. 2–4 are of the two-inlet type having, as in the basic arrangement shown in FIG. 1, two gas inlets 12 and 13 symmetrically formed on one end of the cylinder 10, and a partition wall 11 for defining gas streaming channels 24 and 25 communicating with said gas inlets. In a preferred embodiment, such two-inlet chopper cylinder has a length of about 8–10 cm and an inner diameter of about 10 mm while the sampling tube has an outer diameter of about 3 mm and an inner diameter of about 2 mm.

The flow chopper shown in FIG. 2 is a modification of the basic arrangement shown in FIG. 1. In said modification, a metal sleeve 19a about half as long as the chamber 14 and having an inner diameter adapted to snugly receive the sampling tube is used as a magnetic material while magnetic poles 26a and 26b are disposed facing respectively the parallel halves of the chamber extending through the gas streaming chambers 24 and 25, close to the outer surface of the chopper cylinder 10A on opposite sides of the metal sleeve so as to be opposed thereto. Thus, the opposed surface areas of the metal sleeve and magnetic pole 26a or 26b are larger than in the case of FIG. 1 and hence the magnetic force exerted between them can be correspondingly increased, thereby increasing the rate of swing or oscillation of the flexible fine tube 17.

Referring to FIG. 3 there is shown a flow chopper 10B in which instead of enlarging the magnetic moving element mounted on the flexible fine tube 17 in the chopper cylinder, a similar moving element is disposed close to a magnetic pole 26 outside the cylinder chamber of the flow chopper, thereby providing an increased magnetic force acting on said moving element. To this end, a cylindrical open wall 27 is provided to stand out of the cylinder wall nearer to the inlet channels 24 and 25 of the chopper cylinder 10B and a magnetic element 28 is disposed at a position on an extension of said open wall 27, said element 28 being joined to the front end of a linking rod 29 anchored to the sampling tube 17 at a place relatively nearer to the front end of said tube, whereby the sampling tube 17 is driven. Fitted on the open wall 27 is a fluid-tight cap member 31 having fixed thereto the magnetic pole 26 for attracting the magnetic element 28 to the illustrated position near the open wall 27 from the opposite or below position (not shown), and a return spring 30 for returning the magnetic element to the opposite position when the magnetic element is freed from the magnetic pole 26 as de-energized. Designated at 32 is a stop provided on the cap member 31 for stopping the magnetic element 28 at its return position. If the weight of magnetic element 28 is enough to return downwardly itself, it is possible to swing or oscillate the sampling tube 17 between its two sampling positions without using any return spring, provided that the flow chopper 10 is fixed in the position shown in FIG. 3.

An embodiment shown in FIG. 4 is so designed that the sampling tube 17 is pushed and pulled and swung simultaneously by a crank wheel 33 located at the outside of a cylinder 10C. Thus, the crank wheel 33 angularly and alternately moves in the bi-directions about its axis to swing the sampling tube 17 in a range of angle A, so that the sampling tube 17 is swung, a fluid-tight seal member 22a serving as a fulcrum while sliding in the opening in said seal member, and the free end within the cylinder moving along an arcuate path B. In this embodiment, it is possible for the sampling tube to alternately enter and withdraw from gas streaming channels 24 and 25 communicating with two gas inlets 12 and 13, respectively.

In such crank drive type flow chopper, it is more advantageous to form the sampling tube 17 of a rigid material having no flexibility, since this will facilitate its slide movement along the seal member 22a.

In reference to the flow choppers shown in FIGS. 1 and 2, in the case of providing three or more steaming channels annularly arranged around the axis, the same number of poles are provided and energized in such manner as a stepping motor or induction motor-poles so as to revolute the sampling tube 17 to bring the latter successively to its gas sampling positions.

Figure 7:
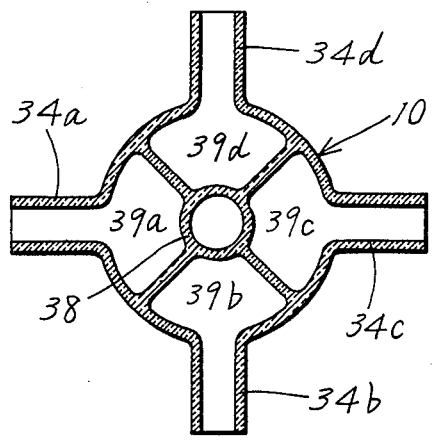
FIG. 7 is a cross sectional view of the inlet channels of the multi-inlet flow choppers shown in FIGS. 5 and 6.

Embodiments in FIGS. 5 and 6 illustrate multi-inlet flow choppers adapted to rotate the sampling tube by an outside motor. In this case, a plurality of gas inlets 34a, 34b, 34c and so on are provided on the upper end of a cylinder 10D or 10E (in this case, the cylinder is preferably upright) and extend radially at right angles with the axis, and a main driving motor 35 is installed on the upper flat end surface of the cylinder through a switch-mechanism 36 having a cam 36a and a switch 36b. The central region of the upper end of the cylinder 10 is opened for receiving the shaft 37 of the motor 35, and there is a sleeve 38 downwardly extending from the opening. Therefore, gas streaming channels 39a, 39c, etc. communicating with the respective gas inlets are formed outside the sleeve 38. The cross-sections of these channels are preferably contiguous sectors as shown in FIG. 7. The front end of the shaft 37 supports a sampling tube driving eccentric disc 40 at a position where it projects sufficiently through the sleeve 38. The front end of the sampling tube 17 is loosely inserted in said eccentric disc 40.

As an intrinsic feature of the embodiment shown in FIG. 5, the sampling tube 17 is bent adjacent the lower end of the cylinder 10D and then extends outwardly through an open wall 41 protruding out of the cylinder-wall. A packing cap 42 is fitted on said open wall 41 to maintain fluid-tightness with respect to the sampling tube 17.

In this embodiment also, the lower end of the cylinder 10D is opened to receive a fine rod 43 which serves to push and pull the front end of the sampling tube 17 in the direction of the axis. The front end of the rod 43 within the cylinder 10 is fixed to the bent portion of the sampling tube 17 by a ring 44, while the other end thereof which projects outside the cylinder is connected to a weight 45 made of a magnetic material. The weight 45 is surrounded with a cup-shaped magnetic pole member 47 fixed to the lower end opening 21a in the cylinder with a packing 46 interposed therebetween. Thus, when the magnetic pole member is energized, the weight is lifted.

With the flow chopper of FIG. 5 arranged in the manner described above, the front end of the sampling tube 17 can be positioned successively in the discharged gas streams by the motor 35 energized by the switch-mechanism 36 while causing it to project into the channels 39a, 39b, 39c and so on, so that only the gas of one channel can be samples at each sampling position.

In the embodiment shown in FIG. 6, the upper structure of the flow chopper cylinder 10E is similar to that shown in FIG. 5, but the sampling tube 17, though somewhat bent, extends downwardly to the outside through a hole 26a at the end of the cylinder. According to this arrangement, the sampling tube 17 is only revoluted by the motor 35, but it is of course possible to push and pull the sampling tube 17 from the outside as in FIG. 5 to cause its front end to project successively into the gas streaming channels.

Particularly for multi-inlet flow chopper cylinders which are increased in size to handle large amounts of gas flow, it is more advantageous from the standpoint of production and use to obtain cylinders by molding of plastics such as acrylic resin than making them of glass. In the embodiments, the inner diameter of the cylinder was about 8cm and its length was about 20 cm, and a sampling tube with an inner diameter of 2 mm and an outer diameter of 3 mm was inserted therein.

Concrete examples of flow chopping type-gas analyzing systems constructed in accordance with analytical objects will now be described.

Figure 8:
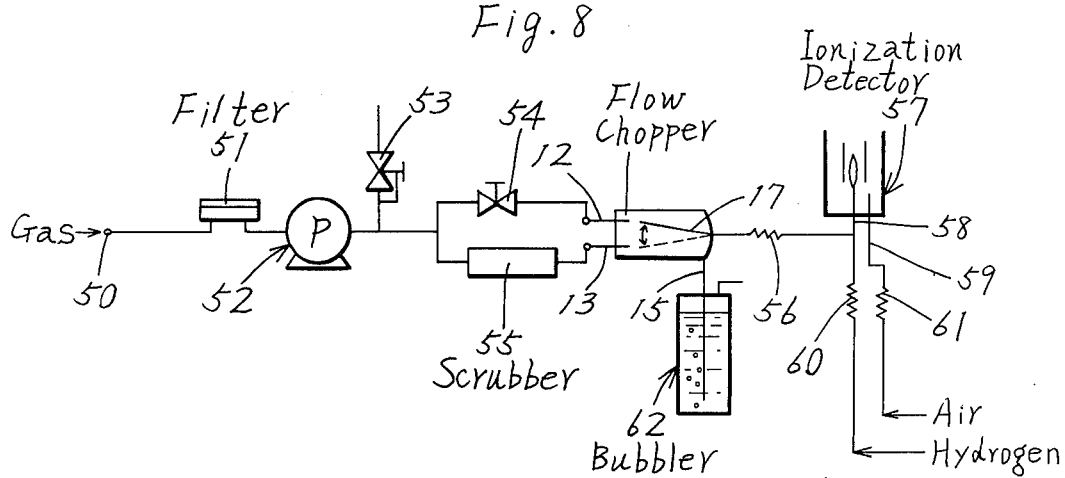
FIG. 8 is a schematic diagram illustrating the flow system of a hydrocarbon analyzer adapted to alternately take a sample gas and a gas which results from removing unsaturated hydrocarbons from the sample gas and send them to a detector, by utilizing a two-inlet flow chopper.

Referring to FIG. 8, there is a flow system embodying the method of the present invention as a hydrocarbon meter adapted to measure unsaturated hydrocarbon concentration to give and indication of air pollution. This hydrocarbon meter comprises a sample gas inlet 50, a filter 51 for removal of dust and dirt, a suction pump 52, a bleed valve 53 placed in a branch, a needle valve 54 placed in a direct line, a column 55 placed in a scrubber line in parallel with said direct line, with these two channels being connected to the two inlet tubes 12 and 13 of a flow chopper 10, respectively. Thus, the flow chopper 10 is of the two-inlet type, and the downstream end of a sampling tube 17 is connected to the fuel gas tube 58 of a hydrogen-flame ionization detector 57 through a fluid resistance tube 56. The fuel gas tube 58 is, of course, supplied with hydrogen gas, into which the sampled gas from the chopper flows. Separate from the fuel gas tube, there is provided an air tube 59 which opens to the lower side of the burner of the detector 57(which opens to the lower side burner of the detector 57.) Designated at 60 and 61 are fluid-resistors placed in the hydrogen gas an air tubes 58 and 59, respectively.

The surplus gas vent 15 of the flow chopper 10, in this case, has a bubbler valve 62 connected thereto, whereby the back pressure in the chopper 10 is controlled and the gases forming the two gas streams are pressed into and sampled by the sampling tube 17 at a constant pressure. The rate of each fractional sampling flow is about ⅓ of the discharged flow of associated channel.

The column 55 placed in the scrubber channel to the flow chopper 10 is filled with, e.g., a perchlorate, whereby the unsaturated hydrocarbons in the sample gas are removed. In this case, the hydrogen-flame ionization detector 57 is supplied alternately through the flow chopper 10 with a sample gas containing total hydrocarbons which has passed through the needle valve 54 which provides the same fluid resistance as that of the paralled column, and gas which contains saturated hydrocarbons but not unsaturated hydrocarbons, so that an ionic current signal due to the directly in coming sample gas and a decrease signal due to the gas deprived from the removal of unsaturated hydrocarbons contributing much to ionic current, alternately appear at the output of the detector 57. In order for the ionization detector to respond sufficiently each gaseous fraction of the gas phases must persist for about 15 seconds.

In addition, another useful scrubber to measure hydrocarbons similar to the one described above is a column filled with granules of manganese dioxide to be heated to about 250° C for burning-off all hydrocarbons except methane in a given gas, if any, while using a hydrogen-flame ionization detector to provide a decrease signal. Further, if a sample gas is passed through soda asbestos or the like to remove carbon dioxide, and then through a nickel catalyst or the like to effect hydrogenation, whereby the carbon oxide in the sample gas is converted into methane, with the detector providing an increase signal.

The detection signals alternately produced in the detector 57 concerning the directly in-coming gas and the scrubbed gas, which, in this case, is an unsaturated-hydrocarbon-removed gas, eventually indicate the concentrations of total hydrocarbons in the sample gas, abbreviated to THC, and of the saturated hydrocarbons, abbreviated to SHC. These signals are mathematically processed in a measuring circuit as shown in FIG. 9 so as to make it possible to indicate the unsaturated hydrocaron, USHC concentration.

Figure 9:
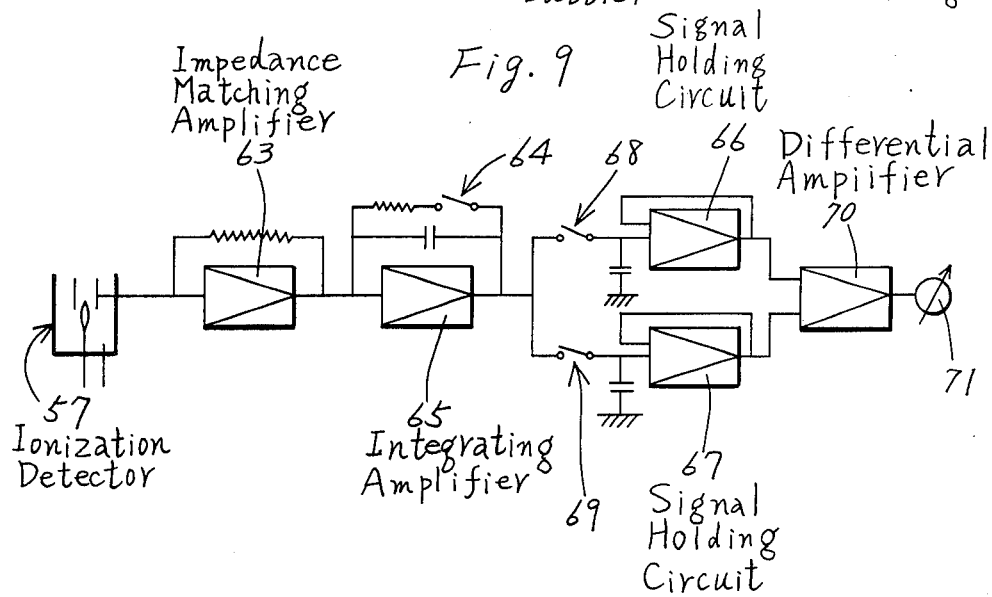
FIG. 9 is a circuit diagram illustrating signal separation and differential detection circuits adapted to be actuated synchronously with the analyzer system shown in FIG. 8.

In FIG. 9, since the output impedance of the hydrogen-flame ionization detector 57 is very low, the output therefrom is first fed into an impedance matching amplifer 63, whose amplified output is supplied to an integrating amplifier 65 having a sampling switch 64. In this case, the fact that the sampling amplifier 65 is an integrating amplifier assures that a signal which is smoothed with respect to random noise will be obtained, so that sensitivity is much higher than in the conventional direct measurement method.

The sampling amplifier 65 has as many output taps as the flow chopper channels, and in this case the output is fed to two signal holding circuits 66 and 67 in synchronism with the flow chopping period, more specifically the period of gas supply to the burner of the detector 57. Switches 68 and 69 connected to the inputs of the holding circuits 66 and 67, respectively, are gate switches for this purpose. The holding circuits 66 and 67 produces dc outputs, which are fed to the two input terminals of a differential amplifier 70, whose differential output, i.e., USHC signal is indicated by an indicator 71.

Figure 10:
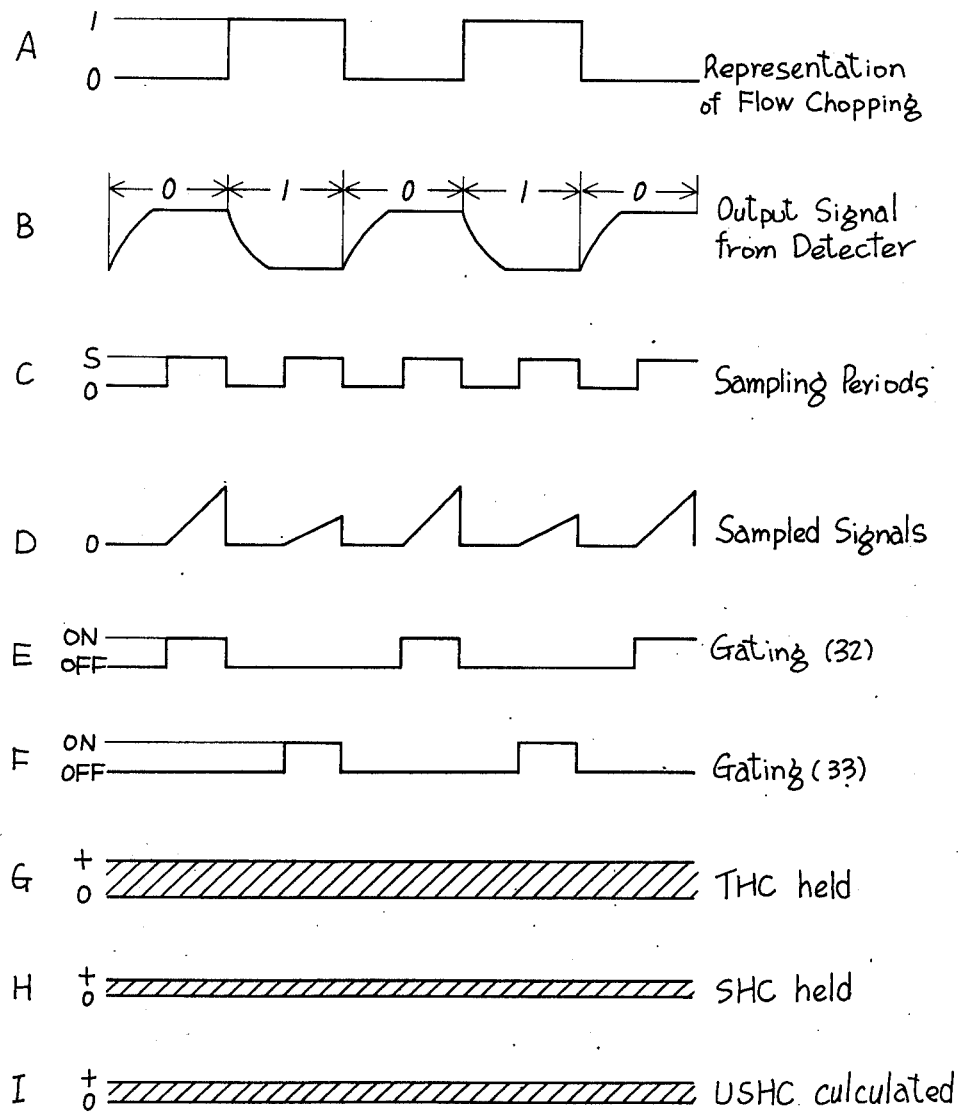
FIG. 10 is timing diagram showing the operations of various parts and signal waveforms in the gas analyzer and signal detecting system shown in FIGS. 8 and 9.

FIG. 10 shows a A-I the periodic waveforms in various portions of the electric circuit shown in FIG. 9 in synchronism with the flow chopping. In FIG. 10, the graph A shows the directly incoming sample gas sampling time represented by level "0" and the USHC-removed gas sampling time represented by level"1", and the graph B shows the output waveform from the detector 57 and hence the impedance matching amplifier 63 which appears in response thereto. The graph C shows the sampling cycles S established by the switch 64 of the sampling amplifier 65. This sampling cycles are made to coincide with the principal portions of the detection signal exclusive of the initial portions of the upper and lower flat levels so that it may correspond to the period in which the sample gas is securely fed to the flame of the burner. Thus, the output from the sampling amplifier, i.e., the integrating amplifier 65 represents the interval integration of the detection signal concerning the corresponding gas during the sampling period, as shown in the graph D. The graphs E and F show the conduction cycles of the gates 68 and 69, respectively. The respective gating cycles are synchronized with the directly in coming THC sampling cycles and the USHC-removed, i.e., SHC gas sampling cycles. Thus, the holding circuit 66 produces a THC held signal which forms a relatively high dc level G and an SHC held signal which forms a relatively low dc level H, and the differential amplifier 70 provides a signal I indicating USHC=THC −SHC, i.e., the unsaturated hydrocarbon concentration in the sample gas.

As the above method of measuring the concentration of hydrocarbons according to the invention is compared with the two-channel differential type ionization detector measurement system disclosed in Japanese Pat. No. 753,917, which is an invention made by us and is being used as by hydrocarbon meter, there is no problem of troublesome and difficult control for coincidence between the response characteristics of two-channel type hydrogen-flame ionization detecting units. As a result, while maintaining high sensitivity and high response characteristics, the present method simplifies the mechanism and operation and assures more accurate analysis.

Figure 11:
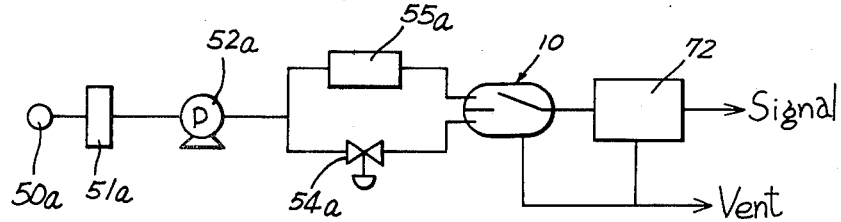
FIG. 11 is a schematic diagram of a carbon dioxide analyzer having a flow system similar to that shown in FIG. 8.

Referring to FIG. 11, there is shown the arrangement of the method of the invention as applied to a carbon monoxide meter, wherein arranged from upstream to downstream are a sample gas inlet 50a, a filter 51a and a suction pump 52a. The gas from the suction pump 52a is introduced into a column 55a and a needle valve 54a placed in a directly in-coming gas line parallel with said column 55a, with said column 55a and needle valve 54a leading to a flow chopper 10. In this embodiment, the arrangement ranging from the inlet 50a to the flow chopper 10 is substantially the same as the hydrocarbon meter shown in FIG. 8 except for the column filler. The detector to be connected to the sampling tube of the flow chopper 10 may, in this case, be a nondispersion infrared gas analyzer 72 capable of directly indicating CO concentration with high sensitivity. In order for this type of analyzer to respond to each gaseous phase, the latter must persist therein for about 30 seconds.

According to the arrangement of this CO analyzer, the column 55a is filled with a catalyst for oxidation, for example, platinum or asbestos, to oxidize the CO in a sample gas to $CO_2$, which is then fed as a zero reference gas to the flow chopper 10 alternating with the directly in coming sample gas. Therefore, the troublesome step is not required, as in the conventional measuring system, of passing the sample gas through a cooler after wetting in order to eliminate the effects of its moisture content prior to feeding the gas to the detector, since the directly in coming gas and the zero reference gas contain equal amounts of moisture, the differential value therefrom is such that the effects of moisture have been completely eliminated, so that the accurate CO concentration can be determined.

Figure 12:
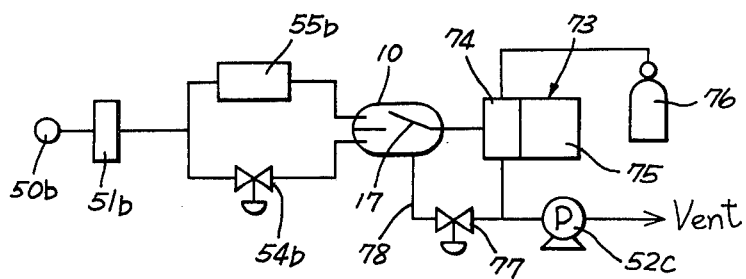
FIG. 12 is a schematic diagram illustrating the flow system of a chemiluminescence gas analyzer using the two-inlet chopper.

Referring to FIG. 12, there is shown the arrangement of the method of the invention as applied to an ozone meter comprising a sample gas inlet 50b, a filter 51b, a scrubber 55b filled with activated charcoal, a needle valve 54b parallel with said scrubber 55b for introducing the sample directly into a flow chopper 10 having two inlets. Designated at 73 is a chemiluminescence detector consisting of a photochemical reaction chamber 74 connected to the sampling tube 17 of the chopper 10, and a photomultiplier 75. In this case also, each gaseous phase must persist in the reaction chamber 74 for at least about 15 seconds. The reaction chamber 74 is fed with ethylene gas from a bomb 76, and the radiation of luminescence resulting from reaction between the ethylene gas and ozone passes through a light-permeable window represented by the partition line between the reaction chamber 74 and the photomultiplier 75 and strikes the photomultiplier. In this case, the sample gas is sucked by a suction pump 52c connected to the vent line extending from the reaction chamber 74, while the suction pressure in the chopping sampling tube 17 is controlled by the flow of gas streamed into a chopper-vent line 78 connected to the pump 52c through a valve 77. The reason why the sampling of gas into the ozone meter is effected by sucking through the detector from a pump, as described above, is that even if the shock applied to $O_3$ when the $O_3$ passes through the pump decomposes $O_3$ into $O_2$, the $O_3$ as a reactant is directly supplied to the detector before the decomposition occurs. In this sense, the mesh size of the filter 51b is considerably restricted.

In the case of this ozone meter also, there is obtained a zero reference and comprising $O_2$ decomposed from $O_3$ interposed in the reference line, through the activated charcoal scrubber 55b thereby permitting the measurement of $O_3$ in which the background formed by other elements than $O_3$ or the effects of noise of the direct line have been completely subtracted by that of the reference line.

In the gas analyzing system described above using the flow chopper of the present invention, the arrangement for alternately feeding a sample gas and the scrubbed gas having left a particular-component to a twin analyzing unit makes the apparatus simple as compared with the so-called two-channel detection system which determines a similiar output difference, and there is no need for operations to provide coincidence and calibration between the two units and between the twin gas channels. Further, as compared with a single-channel analyzer in which usually a zero gas for zero reference is fed in the first place and then a sample gas is fed, in the present invention the effects of noise and background can be completely eliminated by performing subtraction using alternate detection values corresponding to the respective gaseous phases. And, as shown in FIG. 9, if an integrating amplifier is placed after the detector, random noise is smoothed, so that the sensitivity is much greater than in the direct measurement method.

Figure 13:
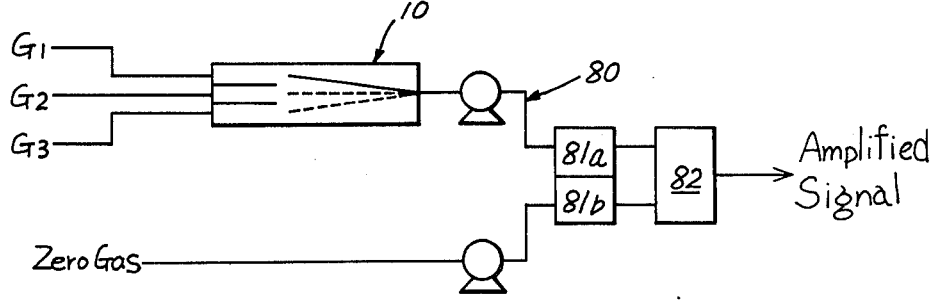
FIG. 13 is a diagram illustrating the flow system of a non-dispersion type infrared gas analyzing system using a multi-inlet flow chopper.

FIG. 13 shows an arrangement wherein a three-inlet flow chopper according to the invention is placed in the sampling channel of a conventional two-inlet gas analyzer 80 and sample gases G1, G2 and G3 are introduced into the three inlet channels of the flow chopper and then into a sample-detecting unit 81a, while the reference or zero gas line connected to a reference-detecting unit 81b, the outputs therefrom being processed in the output terminals of the pair of units 81a and 81b themselves or in a differential amplifier 82, thereby determining the value of each sample gas with respect to the zero gas, namely the substance-concentrations in question simultaneously (in a synchronously selected manner, of course).

According to such measuring system, when the concentrations of different gases are to be measured on the basis of the same zero gas, unlike the conventional practice there is no need of providing a separate measuring system or staggering the time for measurement of the substances in question by a conventional two-channel system. Therefore, the time and trouble involved in measurement are minimized. Further, since measurements are taken on the basis of a zero gas whose conditions remain unchanged and under the same conditions of measuring the zero gas, the concentrations of many gases can be accurately measured by eliminating errors which would otherwise appear randomly at the measurement for each substance in question. For example, by using a multi-inlet chopping system, the detection of the concentrations of same components with respect to each of the gases sampled at many points can be achieved, or by changing the number of stages and kind of scrubbers disposed in respective lines connected to inlet channels which are defined by division in a similar multi-inlet system, the simultaneous measurement of different components in the same sample is made possible wherein the respective components prior to the arrivals at the flow chopper are converted into the increased or decreased amounts of the same component responsive to the same detector and detection signals corresponding to this gaseous sequence are produced at the detector.

What we claim is:

1. An apparatus for collectively sampling a plurality of gases, comprising:

means for introducing a plurality of continuous gas streams simultaneously into a generally closed predetermined space in such a manner as to prevent them from substantially mixing together, a ventilated chamber defining said predetermined space and serving to receive said plurality of gas streams;

a gas sampling tube in said chamber having an inlet end which is permanently opened toward said introduction means, said tube being capable of positioning said inlet end thereof successively in each of said gas streams introduced into said chamber to receive samples of the gas streams, and the other end of said tube adapted to be coupled to downstream analysis equipment for transferring said sample thereto;

means for positioning said inlet end in each of said gas streams; and, a surplus gas exhaust port formed in the downstream region of said chamber for ventilating said chamber.

2. An apparatus as set forth in claim 1 which further includes pressure control means coupled to said surplus gas exhaust port of said chamber for collectively controlling the pressures of the gases to be sampled by said sampling tube.

3. An apparatus as set forth in claim 1 wherein said positioning means comprises a magnetic body operatively connected to said sampling tube, and magnetic-field generating means disposed outside said chamber and capable of magnetizing said magnetic body to position said sampling tube successively into the gas sampling positions.

4. An apparatus as set forth in claim 1 wherein said positioning means comprises a revolution driving mechanism disposed outside said chamber, and means for operatively connecting said driving mechanism to said sampling tube to position said sampling tube successively into gas sampling positions.

5. An apparatus for collectively sampling a plurality of gases, comprising:

means for introducing a plurality of continuous gas streams simultaneously into a generally closed predetermined space so as to prevent them from substantially mixing together;

gas sampling means in the form of a flexible tube disposed in said predetermined space, said gas sampling means having a cross-sectional area of no more than about 1/20 the cross-sectional area of said gas streams, a portion of said tube being restrained and said tube being adapted to be positioned successively in said gas streams, with an end which is unconstrained opened substantially toward said introduction means; and means for positioning said sampling means successively into said gas sampling positions.

6. An apparatus as set forth in claim 5 wherein said gas stream introduction means includes a pair of parallel channels for introducing two continuous gas streams into the predetermined space in essentially parallel streams, and wherein said positioning means includes a driving mechanism for swinging the free end of said sampling tube around its restrained portion to bring said sampling tube successively into alternate gas stream sampling positions.

7. An apparatus as set forth in claim 5 wherein said gas stream introduction means includes at least three parallel channels for introducing at least three continuous gas streams into said predetermined space in essentially parallel streams around a common axis, and wherein said positioning means includes a revolution-driving mechanism for revoluting the free end of said sampling tube around said axis to bring said sampling tube successively into the gas sampling positions.

8. A cylinder for use in collectively sampling a plurality of gases, through which gases are essentially constantly flowing, said cylinder comprising:

a plurality of inlet channels mutually defined at one end of and within the cylinder by axially extending partition walls, each inlet channel communicating with a different gas stream supply line and being opened toward the other end of the cylinder;

an exhaust port formed generally at the other end of said cylinder; and a peripheral wall defining said chamber to form a ventilated chamber communicating said inlet channels with said exhaust port and surrounding a movable gas sampling tube so as to allow said tube to move to gas sampling positions, said gas sampling tube being inserted into the cylinder through a region generally at said other end and having a free end adjacent and opening towards said inlet channels, said sampling tube having an outer diameter smaller than the minimum cross-sectional area of each inlet channel.

said sampling tube being operatively connected to a driving mechanism for successively positioning the opening of the free end of the sampling tube adjacent each said inlet channel.

9. A cylinder as set forth in claim 8, wherein said driving mechanism moves to bring the free open end of said sampling tube successively into each said gas stream in opposed relation thereto and to cause said free open end to project into the corresponding inlet channel.

10. A gas analyzing system comprising:
a plurality of continuous gas stream supplying lines;
a flow chopper which includes means for introducing gas streams supplied from said lines into a predetermined space so as not to substantially mix together, and a gas sampling tube having an inlet permanently opened toward said supplying lines, said sampling tube being adapted to be positioned successively in each gas stream introduced into said space;
a detector coupled to said sampling tube, said detector being sensitive to a predetermined component;
a first circuit for deriving from said detector separate signals corresponding to the successively sampled gases; and
a second circuit for comparing the separate signals corresponding to the respective gaseous phases with each other.

11. A system as set forth in claim 10, wherein said plurality of gas supplying lines comprise a plurality of lines branching off from a single line which supplies a single gas and which includes columns for eliminating a particular component in the gas each column selectively arranged in each of said plurality of lines for permitting the determination of the concentration of said component in the gas.

12. A system according to claim 10, wherein said plurality of gas supplying lines comprise a plurality of lines branching off from a single line which supplies a single gas and which includes columns for converting a first predetermined component into a second component and compensating the fluid resistances in said lines for resultant differences, each said column selectively arranged in each of said plurality of lines for permitting the determination of the concentration of at least one of said first and second components in the gas.

13. A method of sampling a plurality of gases, which comprises the steps of:
forming a plurality of continuous gas streams, each gas stream formed by a different gas;
introducing all of said as streams into a common defined space so that mixing of said gas streams is substantially prevented at least near the point of introduction into the space; and
sequentially sampling predetermined stream lengths of gas from said gas stream through a single sampling conduit positioned within the defined space so that an essentially continuous flow is provided in the conduit, comprising a series of stream lengths of the different gases.

14. A method according to claim 13, wherein the single conduit comprises a relatively slender tube having a cross-sectional area no greater than about 1/20 that of each gas stream throughout generally the entire length of the single conduit located within the space such that disturbance of said gas streams is minimized.

15. A method according to claim 14 wherein the stream length of each different gas in said single tube is at least about twice the inner diameter of said tube, such that a series of gases is taken out of the downstream end of the tube.

16. A method according to claim 14 which further includes the step of providing ventilation in said defined space for enabling said gas streams to flow in an essentially streamline manner along generally the entire length of said tube in said defined space.

17. A method according to claim 16 which further includes the step of controlling the pressure of gases leaving said defined space such that the stream length of the gases flowing into said tube are collectively controlled.

18. A method of gas analysis for a plurality of simultaneously fed gases, which comprises the steps of:
forming a plurality of continuous gas streams, each gas stream formed by a different gas;
introducing all of said gas streams into a common definite space so that mixing of said gas streams is substantially prevented, at least near the point of introduction into said space;
sequentially sampling predetermined stream lengths of gas from said gas streams through a single sampling conduit positioned within the defined space so that an essentially continuous flow is provided in the conduit, comprising a series of stream lengths of the different gases; and
conducting the continuous flow of gas stream lengths to a gas detector which is sensitive to a particular substance, detector adapted to generate a series of signals corresponding to the concentrations of said particular substance in each gas.

19. A method according to claim 18 wherein a signal in said series of signals, which corresponds to a predetermined gas, is used as a reference for comparison with other gases, such that the concentration of a particular substance in each gas is evaluated with respect to the predetermined reference value.

20. A method according to claim 18 wherein the output signals generated by the detector are separated in synchronism with the sampling of the gas streams, and which further includes the steps of amplifying the separated signals corresponding to each gas and individually removing each amplified signal.

21. A method according to claim 20, wherein the output signals generated by the detector are separated in synchronism with the sampling of the gas streams, and which further includes the steps of amplifying the separated signals corresponding to each gas and individually removing each amplified signal.

22. A method according to claim 19 wherein said sampling step comprises alternately sampling a first gas stream containing a predetermined component which is detectable by the detector and a second gas stream which is provided by removing the predetermined component from the first gas stream, to provide an essentially continuous sampling flow which is coupled to the detector, such that the concentration of the predetermined component in the first gas stream can be determined by the difference between the signals generated by the detector, which correspond to the first and second gas streams.

23. A method according to claim 20 wherein the first and second gas streams are sampled under essentially identical conditions except for the removal of the predetermined component.

24. A method of mixing a plurality of gases, which comprises the steps of:
   forming a plurality of continuous gas streams of different gases;
   simultaneously introducing all of said gas streams into a defined space so as to substantially prevent mixing of said gas streams;
   sequentially sampling said gas streams from the defined space, the period of time for sampling each gas stream being selected relative to each other such that the gas streams are sampled in desired proportions.

25. A method for analyzing a gaseous matter, comprising the steps of:
   alternately supplying a sample gas which includes the gaseous matter and a reference gas, to a non-dispersible infrared gas analyzer; and
   measuring the alternate signals generated by the detector, such that the magnitude of the detected character of the gaseous matter can be determined relative to that of the reference gas.

26. An apparatus according to claim 1 wherein said introduction means includes at least one partition wall adapted to define a gas streaming channel for each of the gas streams and wherein said positioning means is adapted to position the inlet end of said gas sampling tube in the gas stream of each streaming channel.

27. An apparatus according to claim 26 wherein said positioning means comprises a magnetic body operatively connected to said sampling tube, and magnetic-field generating means disposed outside said chamber and capable of magnetizing said magnetic body to position said sampling tube successively into the gas sampling positions.

28. An apparatus according to claim 26 wherein said positioning means comprises a revolution driving mechanism disposed outside said chamber, and means for operatively connecting said driving mechanism to said sampling tube to position said inlet end thereof successively into gas sampling positions.

29. An apparatus according to claim 26 wherein said positioning means comprise a crank wheel and drive means therefor located outside said ventilated chamber, said crank wheel adapted to both insert and withdraw the inlet end of said sampling tube into and out of said streaming channels.

30. An apparatus according to claim 1 wherein an essentially fluid-tight seal is formed between said sampling tube and a portion of the ventilated chamber.

31. An apparatus according to claim 3 wherein said magnetic-field generating means includes at least two electromagnetic pole members, positioned on generally opposite sides of the chamber, such that the electromagnetic pole members may be energized to attract and repel the magnetic body for positioning the inlet end of said sampling tube in the desired gas stream.

32. An apparatus according to claim 31 wherein an essentially fluid-tight seal is formed between said sampling tube and a portion of the ventilated chamber.

33. An apparatus according to claim 4 wherein an essentially fluid-tight seal is formed between said sampling tube and a portion of the ventilated chamber.

34. An apparatus according to claim 9 wherein an essentially fluid-tight seal is formed between said sampling tube and the region of said ventilated chamber through which said tube is inserted..

35. A method according to claim 13 wherein said step of sequentially sampling the gases includes sequentially positioning the free end of the sampling conduit in each said gas stream.

36. A method according to claim 35 wherein said step of positioning the free end of the sampling conduit is carried out by applying and varying a magnetic field to a magnetic body attached generally at the free end of the sampling conduit.

37. A method according to claim 36 wherein said step of positioning the free end of the sampling conduit is carried out by a revolution drive mechanism coupled generally at the free end of the sampling conduit and adapted to position the free end of the sampling conduit successively into gas sampling positions.

* * * * *